United States Patent
Zawaideh

(10) Patent No.: US 7,463,355 B1
(45) Date of Patent: Dec. 9, 2008

(54) NONDESTRUCTIVE OPTICAL TECHNIQUE FOR SIMULTANEOUSLY MEASURING OPTICAL CONSTANTS AND THICKNESS OF THIN FILMS

(75) Inventor: Emad Zawaideh, Carlsbad, CA (US)

(73) Assignee: Scientific Computing International, Carlsbad, CA (US)

( * ) Notice: Subject to any disclaimer, the term of this patent is extended or adjusted under 35 U.S.C. 154(b) by 350 days.

(21) Appl. No.: 10/460,089

(22) Filed: Jun. 12, 2003

(51) Int. Cl.
*G01J 4/00* (2006.01)

(52) U.S. Cl. ........................ 356/364; 356/369; 356/367

(58) Field of Classification Search ......... 356/364–369, 356/630, 503–505
See application file for complete search history.

(56) References Cited

U.S. PATENT DOCUMENTS

| | | | | |
|---|---|---|---|---|
| 5,131,752 A | * | 7/1992 | Yu et al. | 356/369 |
| 5,889,592 A | * | 3/1999 | Zawaideh | 356/504 |
| 6,304,326 B1 | * | 10/2001 | Aspnes et al. | 356/369 |
| 6,411,385 B2 | * | 6/2002 | Aspnes et al. | 356/369 |
| 6,567,213 B2 | * | 5/2003 | Rosencwaig et al. | 359/369 |
| 6,590,656 B2 | * | 7/2003 | Xu et al. | 356/369 |
| 6,654,131 B2 | * | 11/2003 | Opsal et al. | 356/625 |
| 6,713,753 B1 | * | 3/2004 | Rovira et al. | 250/225 |
| 6,774,997 B2 | * | 8/2004 | Rosencwaig et al. | 356/369 |
| 6,822,738 B1 | * | 11/2004 | Johs et al. | 356/369 |
| 2003/0076497 A1 | * | 4/2003 | Wolf et al. | 356/369 |
| 2004/0265477 A1 | * | 12/2004 | Nabatova-Gabain et al. | 427/10 |

OTHER PUBLICATIONS

E. Elizalde et al, Determination of thickness and optical constants of thin films from photometric and ellipsometric measurements, Dec. 1986, Applied Optics, vol. 25, No. 24.*

Cao et al, Simultaneous determination of the optical constants and thickness of very thin films by using soft-x-ray reflectance measurements, Apr. 1994, vol. 33, No. 10.*

\* cited by examiner

*Primary Examiner*—L. G Lauchman

(57) ABSTRACT

Optical systems and methods that simultaneously measure optical constants (n, k) and thickness of thin films. The systems and methods use of differential polarimetry (differential analysis of spectroscopic multi-angle reflection and ellipsometric data) to measure optical constants (n k) and thickness of ultra-thin films.

17 Claims, 5 Drawing Sheets

NONDESTRUCTIVE OPTICAL TECHNIQUE FOR SIMULTANEOUSLY MEASURING OPTICAL CONSTANTS AND THICKNESS OF THIN FILMS

BACKGROUND

The present invention relates to optical measuring systems and methods, and more particularly to nondestructive optical systems and methods for simultaneously measuring optical constants (n, k) and thickness of thin films.

There are several known methods for determining the optical constants and thickness of thin films. One conventional method is disclosed in "Handbook of Optical Constants of Solids", edited by E. D. Palik (academic Press, N.Y., 1985). This method measures normal-incidence reflectance and transmittance over a wide spectral range.

Another conventional method is disclosed in "Handbook of Optical Constants of Solids II", edited by E. D. Palik (Academic Press, N.Y., 1991). This method measures R and T for normal and oblique angles of incidence (45'; 60') for the polarizations TE and TM, over a wide spectral range.

Another conventional method is disclosed by O. S. Heavens in "Physics of Thin Films", Vol. 2, edited by G. Hass and R. E. Thum (Academic Press, N.Y., 1964). This method uses ellipsometry to measurement the polarization states of collimated monochromatic light before and after reflection from a surface to obtain the ratio $\rho = r_p/r_s = \tan \psi \exp(i \Delta)$ of the complex p and s reflection coefficients.

However, for very thin films (on the order of a few atomic layers), these methods are not capable of measuring the optical constants (n and k) and thickness independently, and at times yield inaccurate results. A major disadvantage of these conventional methods is that the optical constants and thickness are coupled and for very thin films they cannot be decoupled or measured independently.

Accordingly, it would be advantageous to have systems and methods for measuring the thickness and optical constants of very thin films independently.

SUMMARY OF THE INVENTION

The present invention overcomes the difficulties of the above-described conventional methods and provides for systems and methods that use multi-angle differential polarimetry to decouple the measurement of the thickness and dielectric function of thin films. The present invention may be used to independently measure the thickness and optical constants of very thin films. The present systems and methods are particularly applicable to very thin films, where the thickness of the film is much less than $\lambda/4$.

An exemplary and preferred embodiment of the system comprises a first light source that emits light that is directed at an oblique angle toward the thin film. A rotating polarizer and a rotating compensator are each disposed at the oblique angle between the first light source and the thin film. A first detector detects light derived from the first light source that is reflected from the thin film BS is disposed at an oblique angle that is complementary to the oblique angle between the incident ray on the thin film surface and the normal vector of the thin film surface. An rotating analyzer is disposed at the complementary oblique angle between the first detector and the thin film.

A second light source emits light that is incident at a normal angle upon the thin film. A second detector is disposed to detect light derived from the second light source that is reflected from the thin film. A controller is coupled to the light sources and detectors. A computer coupled to outputs of the first and second detectors that implements an algorithm that simultaneously measures the optical constants (n, k) and the thickness of the thin film using multi-angle differential polarimetry.

The present systems and methods measure normal incident reflectance and ellipsometric parameters at oblique angles of incidence (for example 70) over a wide spectral range, using, for example, a spectrophotometer and then applying the following exemplary methodology to determine the optical constants (n, k) and thickness of a thin film that is disposed on a substrate.

The first step is to measure normal incident reflection spectra (R) and ellipsometric parameters at an oblique angle ρ as a function of frequency.

The second step is to determine the theoretical value of R and p for the substrate ($R_s$ and $p_s$).

The third step is to define new normalized parameters:

$$\xi_0 \equiv \frac{R - R_s}{R_s}, \xi_1 \equiv \frac{\rho - \rho_s}{\rho_s}, \text{ and } R\xi \equiv \frac{\xi_0}{\xi_1}.$$

The fourth step is to model the unknown optical constants using a general dispersion formula that is capable of describing the dispersion in the optical constants (n, k) in the measured wavelength range.

The final step is to determine the thicknesses and coefficients of the dispersion formula (optical constants) of the unknown layers. Nonlinear global optimization algorithms may be used in the final step to minimize the merit function (loss function or error function) of experimental and theoretical data.

BRIEF DESCRIPTION OF THE DRAWINGS

The various features and advantages of the present invention may be more readily understood with reference to the following detailed description taken in conjunction with the accompanying drawings, described by way of example, and wherein like reference numerals designate like structural elements, and in which.

DETAILED DESCRIPTION

Figure 1:
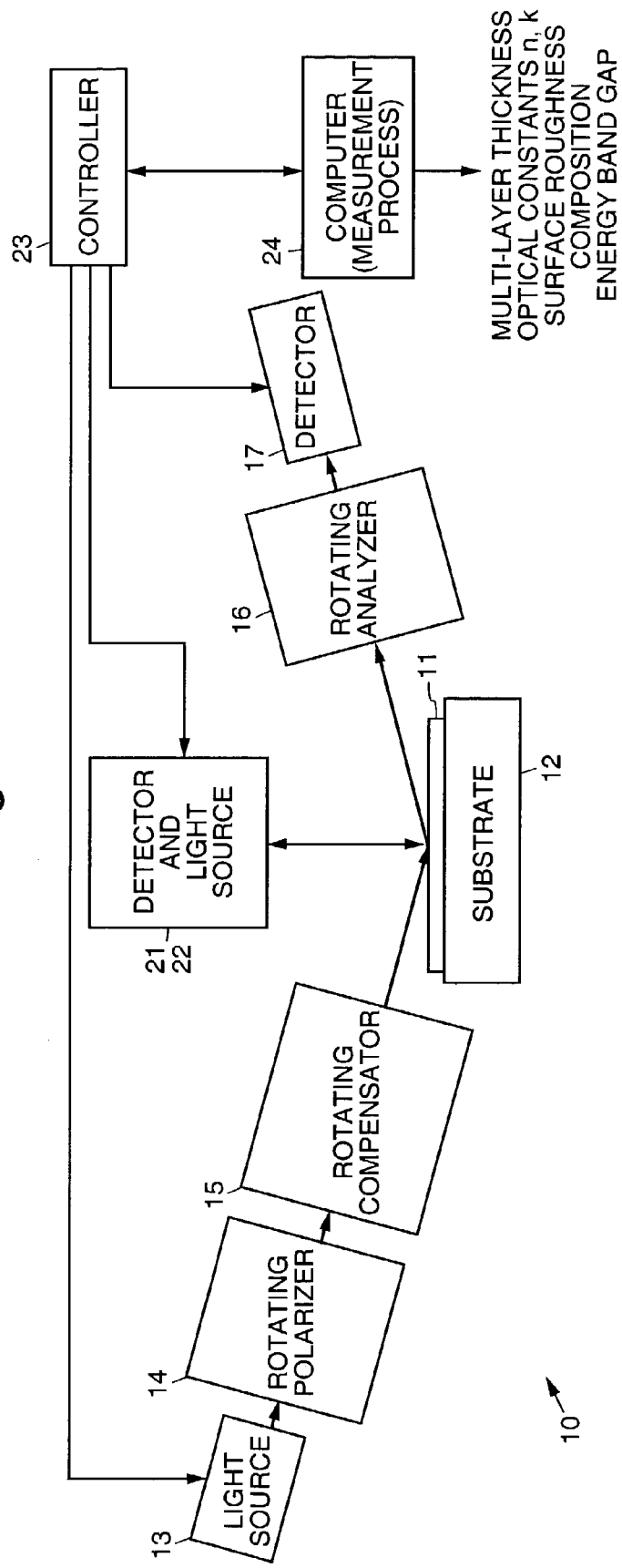
FIG. 1 illustrates an exemplary measurement system in accordance with the principles of the present invention.

Referring to the drawing figures, FIG. 1 illustrates an exemplary measurement system 10 in accordance with the principles of the present invention. The exemplary measurement system 10 comprises a first light source 13 that emits light that is incident at an oblique angle upon a thin film 11 disposed on a substrate 12. The light that is emitted by the first light source 13 passes through a (fixed or rotating) polarizer 14 and an optional (fixed or rotating) compensator 15 (fixed or rotating retarder 15) prior to impinging upon the thin film 11. The rotating polarizer 14 operates to linearly polarize the incident beam. The optional (fixed or rotating) compensator 15 operates to elliptically polarize the incident beam.

The light that is emitted from the first light source 13 and reflected from the thin film 11 passes through a (fixed or rotating) analyzer 16 and is detected by a first detector 17 that is disposed at an oblique angle that is complementary to the oblique angle that the light is incident upon the thin film 11. The (fixed or rotating) analyzer 16 operates to transmit light of known linear polarization. A second light source 21 and a second detector 22 are disposed above the thin film 11. The second light source 21 emits light that is incident substantially normal to the thin film 11 (angle of incidence is typically less than 7 degrees with respect to normal vector of thin film surface), which is detected by the second detector 22.

A controller 23 is coupled to the first and second light sources 13, 21 and the first and second detectors 14, 22. A computer 24 that implements an algorithm 30 implementing a process 30 or method 30 in accordance with the principles of the present invention is coupled to outputs of the first and second detectors 13, 21. The process 30 or method 30 implemented in the computer 24 simultaneously measures optical constants (n, k) and the thickness of the thin film 11. Outputs of the computer 26 include the thickness of a multilayer thin film 11, the optical constants n and k, surface roughness, the composition of the thin film 11, and the energy band gap (composition of the thin film and energy bandgap are possible output(s) if one chooses a dispersion model which requires these parameter(s) as input in order to calculate the optical constants, n and k).

It is to be understood that the compensator 15 is used in a preferred embodiment of the present invention, and it is not necessary that the compensator 15 rotate. Also, the compensator 15 is not necessary to collect ellipsometric data. The compensator 15 helps reduce signal to noise in the measured parameters whenever delta is close to zero or 180 degrees, which is often the case when measuring very thin films 11 deposited on silicon or glass substrates 12.

There are many ways to collect ellipsometric data. For example, ellipsometric data may be obtained using (a) a rotating analyzer and a fixed polarizer, (b) a rotating polarizer and a fixed analyzer, (c) a fixed polarizer, a fixed analyzer and a rotating compensator, or (d) a fixed polarizer, a fixed analyzer, and an electrically controlled (non-rotating) compensator. Sometimes this is referred to as a phase modulated ellipsometer. This class of ellipsometer is perhaps the most sensitive ellipsometer that is currently available.

Typically during the collection of ellipsometric data, only one component is varied. The present invention may employ a rotating analyzer, a rotating polarizer, and a rotating compensator. It is to be understood that this does not mean that all of these are rotating simultaneously during measurement. However, it is desirable if all of these devices can be rotated, since with some prior knowledge of approximate film/substrate parameters, maximum sensitivity can be achieved by fixing those components(s) that are fixed during the measurement to values that are calculated by a controlling program, for example.

It is to be understood that the present invention may employ any method of collecting ellipsometric data or polarized oblique reflection data. What is particularly unique and new in the present invention is how the ellipsometric or polarized oblique reflection data is combined with reflection data at normal incidence to extract optical constants and thickness.

Figure 2:
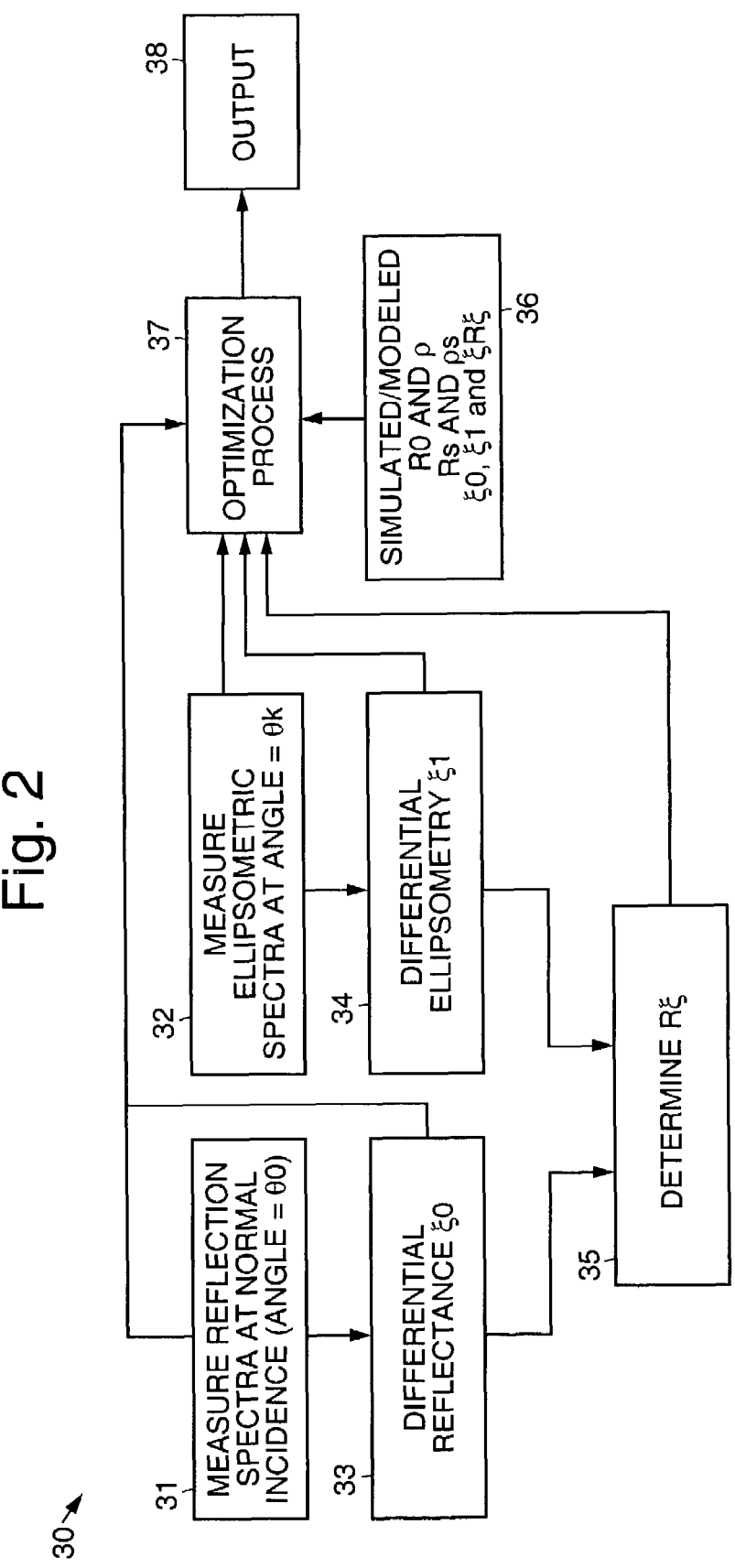
FIG. 2 is a flow chart that illustrates an exemplary measurement and calculation process in accordance with the principles of the present invention.

The present systems 10 and methods 30 measure normal incident reflectance and ellipsometric parameters at oblique angles of incidence (70 degrees, for example) over a wide spectral range, using a spectrophotometer, for example (comprising the first and second light sources, 13 21 and the first and second detectors 14, 22), and then applying the following methodology 30 to determine the optical constants (n, k) and thickness of the thin film 11. Referring to FIG. 2, it is a flow chart that illustrates an exemplary measurement and calculation process 30 of method 30 in accordance with the principles of the present invention.

The first step is to measure 31 normal incident reflection spectra (R) as a function of frequency. The next step is to measure 32 ellipsometric parameters at an oblique angle ρ as a function of frequency.

The next step is to determine the theoretical value of R and ρ for the substrate 12 ($R_s$ and $p_s$).

The next step is to determine 33, 34, 35 new normalized parameters, given by:

$$\xi_0 \equiv \frac{R - R_s}{R_s}, \xi_1 \equiv \frac{\rho - \rho_s}{\rho_s}, \text{ and } R\xi \equiv \frac{\xi_0}{\xi_1}.$$

The next step is to model 36 the unknown optical constants using a general dispersion formula that is capable of describing the dispersion in the optical constants (n, k) in the measured wavelength range. Exemplary general dispersion formulas are disclosed by G. E. Jelison, Jr. and F. A. Modine "Parameterization of the optical functions of amorphous materials in the interband region" Applied Physics Letters 69 (3), 15 Jul. 1996, and Applied Physics Letters 69 (14), 30 Sep. 1996, and in U.S. Pat. No. 5,889,592 issued Mar. 30, 1999, for example.

The final step is to determine 37 the thickness of the thin film 11 and coefficients of the dispersion formula (optical constants) of the unknown layers of the thin film 11. Nonlinear-global optimization algorithms may be used to minimize a merit function (loss function or error function) of experimental and theoretical data:

$\xi_0(\rho), \xi_1(\rho)$ and $R\xi((\rho))$.

Figure 3:
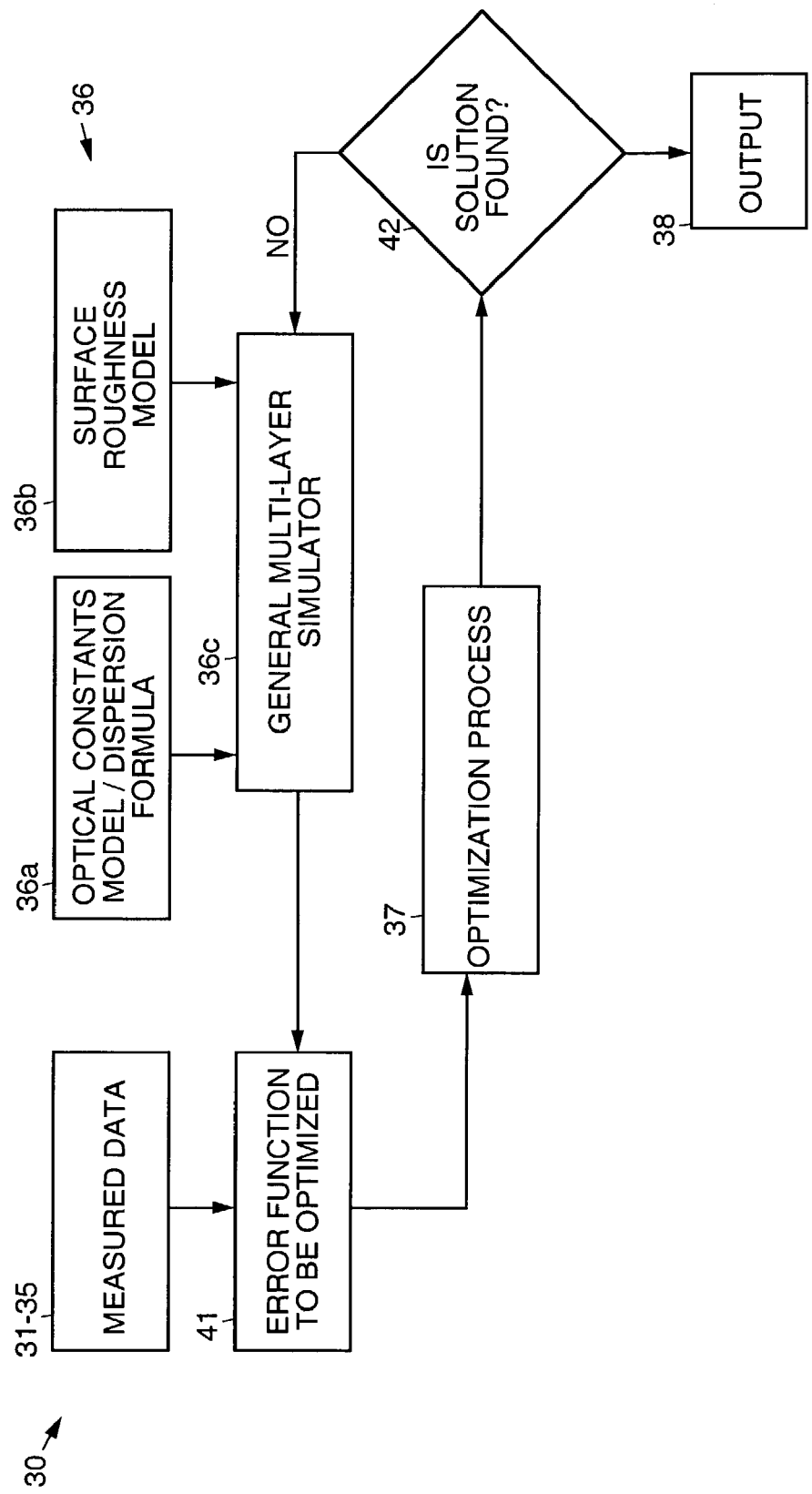
FIG. 3 is a flow chart that illustrates details of the calculation process shown in FIG. 2.
Figure 4:
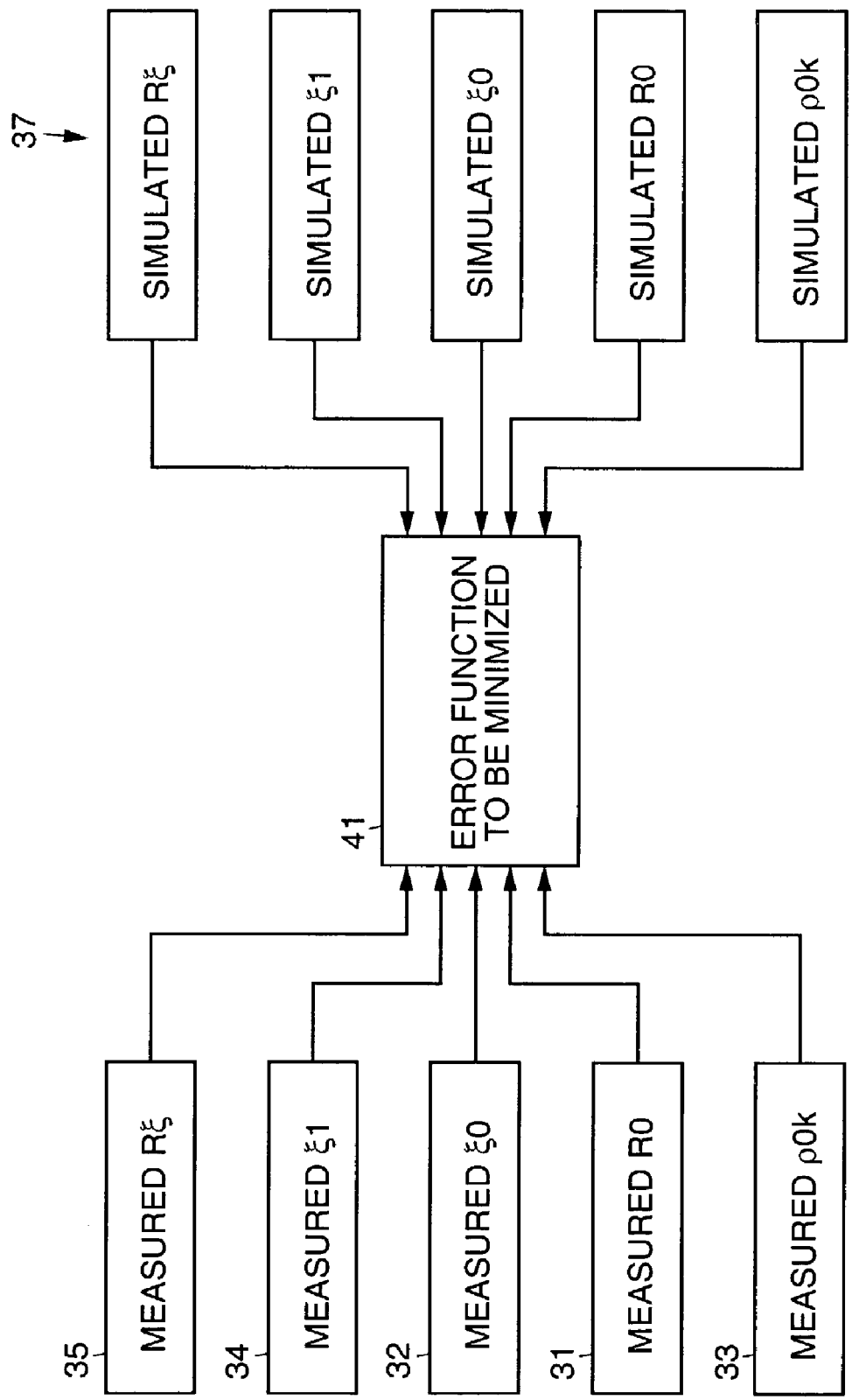
FIG. 4 is a flow chart showing input variables used to define the error function (penalty function)

FIG. 3 is a flow chart that illustrates details of the calculation process 30 shown in FIG. 2, and in particular illustrates the use of error functions that are optimized to determine the thickness of the thin film 11 and coefficients of the dispersion formula. FIG. 4 is a flow chart showing input variables used to define the error function 41 (penalty function 41).

Thus, as is shown in FIG. 3, the measured spectroscopic data determined in steps 31-35 are input to an error function 41 that is to be optimized. An optical constants model and dispersion formula 36a and surface roughness model 36b (comprising the model 36) are input to a multi-layer simulator 36c. Outputs of the multi-layer simulator 36c are input to the error function 41 that is to be optimized. Outputs of the error function 41 are input to the optimization process to determine 37 the thickness of the thin film 11 and coefficients of the dispersion formula (optical constants) of the unknown layers of the thin film 11. Optimization continues 47 until a solution is found, whereafter the data is output 38.

Depending on the optimization technique used, a single merit function may be defined for all the data, namely:

$$\text{Merit Function} = \left[ \sum_{j=1}^{n} \left[ |Y_{\exp_j} - Y_{calculated_j}|^\beta \times \text{weight}_j \right] \right]^{\frac{1}{\beta}}$$

where $Y_{\exp\,j}$ and $Y_{calculated\,j}$ represent the experimental and calculated (simulated) data of parameter j, and $\beta=1, 2$ for absolute deviation and least square options, respectively. On the other hand, for gradient optimization methods, each fitted parameter has its own merit function that is minimized, namely:

$$(\text{Merit Function})_j = \left[|Y_{target_j} - Y_{calculated_j}|^\beta \times \text{weight}_j\right]^{\frac{1}{\beta}}.$$

To illustrate the significance of the present method 30 (and system 10) consider a simple example case of a very thin single isotropic film 11 with thickness $d \ll \lambda$ on a semi-infinite substrate 12 (e.g. a silicon wafer) measured in air (vacuum). The normal incident reflectance reduces to:

$$R \approx R_S(1 + df_1(\varepsilon))$$
$$\xi_0 \equiv \frac{R - R_s}{R_s} \approx df_1(\varepsilon)$$

To first order $f_1(\varepsilon)$ is only a function of the complex dielectric function of the film and the substrate.

$$\rho \approx \rho_S(1 + df_2(\varepsilon)), \text{ and } \xi_1 \equiv \frac{\rho - \rho_s}{\rho_s} \approx df_2(\varepsilon).$$

To first order $f_2(\varepsilon)$ is only a function of the complex dielectric function of the film and the substrate.

The ratio of the $\xi_0$ to $\xi_1$ is given by $$R\zeta \equiv \frac{\zeta_1}{\zeta_0} \approx \frac{f_1(\varepsilon)}{f_2(\varepsilon)}$$

Note that to first order $R\xi(\rho)$ is not a function of thickness and only a function complex dielectric function of the film and the substrate. Thus the optical property of the thin film 11 and its thickness can be independently determined, given by:

$$d = \frac{\zeta_0}{f_2(\varepsilon)}.$$

Figure 5:
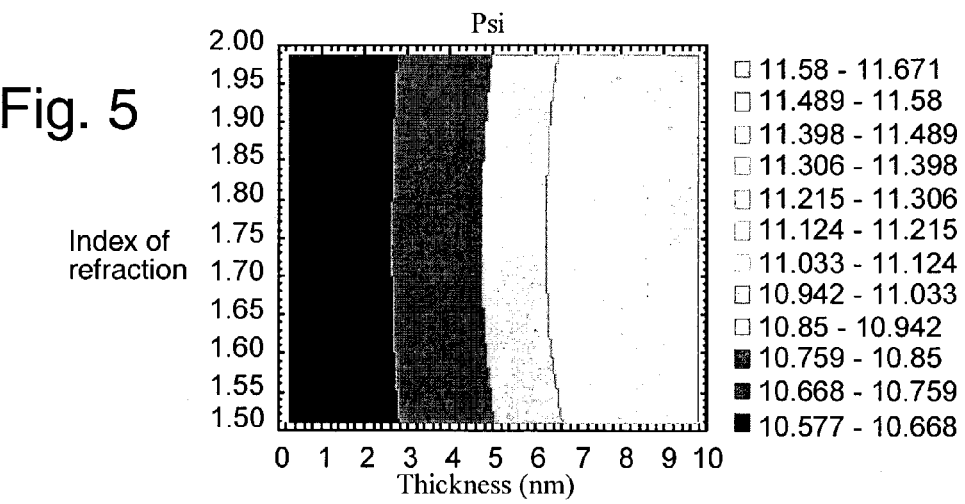
FIG. 5 shows simulated normal incidence reflection as a function of index of refraction and thickness of film on a silicon substrate.
Figure 6:
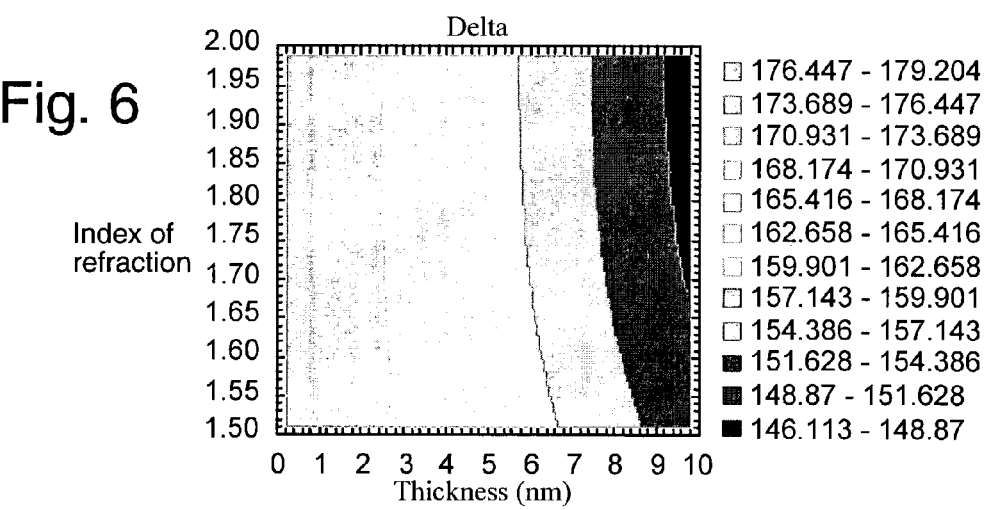
FIG. 6 shows simulated ellipsometric parameter delta (Δ at 70 degrees) as a function of index of refraction and thickness of film on a silicon substrate.
Figure 7:
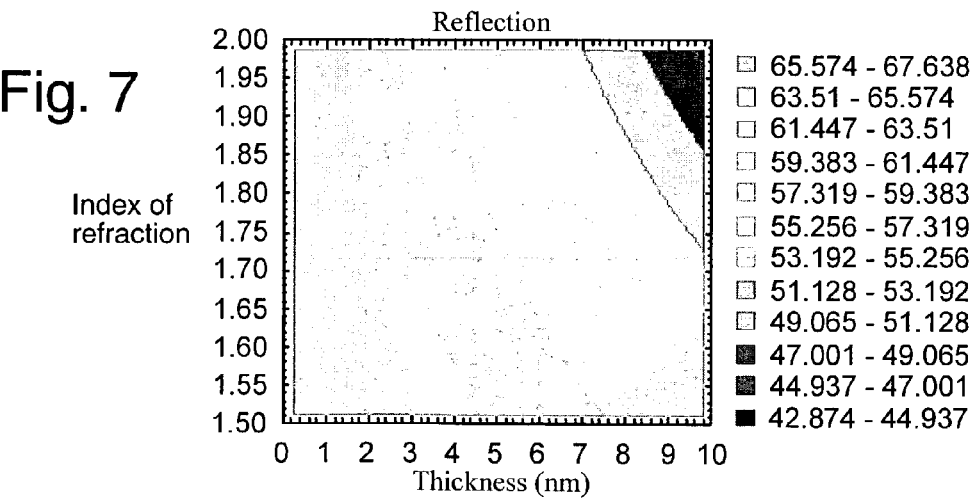
FIG. 7 shows simulated ellipsometric parameter psi (ψ at 70 degrees) as a function of index of refraction and thickness of film on a silicon substrate.

FIGS. 5-7 illustrates that the difference in functional dependence of the ellipsometric and reflection data. FIG. 5 shows simulated normal incidence reflection as a function of index of refraction and thickness of film on a silicon substrate. FIG. 6 shows simulated ellipsometric parameter delta ($\Delta$ at 70 degrees) as a function of index of refraction and thickness of film on a silicon substrate. FIG. 7 shows simulated ellipsometric parameter psi ($\psi$ at 70 degrees) as a function of index of refraction and thickness of film on a silicon substrate.

In general, the present invention does not impose any constraint on the value of wavelength dependence of index of refraction or extinction coefficient of the measured thin film 11. The optical constants are modeled using a dispersion formula that accurately models the optical constants in the measured wavelength range. Multiple angles may be used for consistency check and higher accuracy.

From the above, it can be seen that the multi-angle differential polarimetry employed in the present systems 10 and methods 30 measures thickness and index independently, measure n and k for very thin films, and can measure multi-layer stacks of thin films 11.

Thus, nondestructive optical systems and methods for simultaneously measuring optical constants (n, k) and thickness of thin films have been disclosed. It is to be understood that the described embodiments are merely illustrative of some of the many specific embodiments that represent applications of the principles of the present invention. Clearly, numerous and other arrangements can be readily devised by those skilled in the art without departing from the scope of the invention.

What is claimed is:

1. A system for simultaneously measuring optical constants (n, k) and thickness of a thin film formed on a substrate, comprising:

a first light source that emits light that is directed at an oblique angle toward the thin film;

a polarizer that disposed at the oblique angle between the first light source and the thin film;

a first detector disposed to detect light derived from the first light source that is reflected from the thin film that is disposed at an oblique angle that is complementary to the oblique angle that the light is incident upon the thin film;

an analyzer disposed at the complementary oblique angle between the first detector and the thin film;

a second light source that emits light that is incident at a normal angle upon the thin film;

a second detector disposed to detect light derived from the second light source that is reflected from the thin film; and a computer coupled to outputs of the first and second detectors that implements an algorithm that simultaneously measures the optical constants (n, k) and the thickness of the thin film using multi-angle differential polarimetry by computing ratios of the change in ellipsometric parameters and reflectance of the thin film relative to the substrate.

2. The system recited in claim 1 wherein the thin film comprises a multilayer thin film.

3. The system recited in claim 1 wherein the computer further determines surface roughness of the thin film.

4. The system recited in claim 1 wherein the computer further determines the composition of the thin film.

5. The system recited in claim 1 wherein the computer further determines the energy band gap of the thin film.

6. The system recited in claim 1 wherein the algorithm implemented in the computer:

measures normal incident reflection spectra (R) of the thin film as a function of frequency;

measures ellipsometric parameters of the thin film at an oblique angle $\rho$ as a function of frequency;

determines theoretical values of R and $\rho$ ($R_s$ and $\rho_s$) for the substrate;

determines new normalized parameters, given by:

$$\xi_0 \equiv \frac{R - R_s}{R_s}, \xi_1 \equiv \frac{\rho - \rho_s}{\rho_s}, \text{ and } R\xi \equiv \frac{\xi_0}{\xi_1};$$

models the unknown optical constants using a general dispersion formula that describes the dispersion in the optical constants (n, k) in the measured wavelength range; and determines the thickness of the thin film and coefficients of the dispersion formula, comprising the optical constants of the unknown layers of the thin film.

7. The system recited in claim 1 further comprising a compensator that is disposed at the oblique angle between the first light source and the thin film.

8. The system recited in claim 7 wherein the compensator comprises a rotating compensator.

9. The system recited in claim 7 wherein the polarizer comprises a fixed polarizer and the analyzer comprises a rotating analyzer.

10. The system recited in claim 7 wherein the polarizer comprises a rotating polarizer and the analyzer comprises a fixed analyzer.

11. The system recited in claim 7 further comprising a controller coupled to the first and second light sources and the first and second detectors.

12. The system recited in claim 7 wherein the polarizer comprises a fixed polarizer, the analyzer comprises a fixed analyzer, and wherein the system further comprises a rotating compensator disposed at the oblique angle between the first light source and the thin film.

13. The system recited in claim 7 wherein the polarizer comprises a fixed polarizer, the analyzer comprises a fixed analyzer, and wherein the system further comprises an electrically controlled non-rotating compensator disposed at the oblique angle between the first light source and the thin film.

14. A method for simultaneously measuring optical constants (n, k) and thickness of a thin film disposed on a substrate, comprising the steps of:
  measuring normal incident reflection spectra (R) of the thin film as a function of frequency;
  measuring ellipsometric parameters of the thin film at an oblique angle ρ as a function of frequency;
  determining theoretical values of R and ρ ($R_s$ and $p_s$) for the substrate;
  determining new normalized parameters, given by:

$$\xi_0 \equiv \frac{R - R_s}{R_s}, \xi_1 \equiv \frac{\rho - \rho_s}{\rho_s}, \text{ and } R\xi \equiv \frac{\xi_0}{\xi_1};$$

modeling the unknown optical constants using a general dispersion formula that describes the dispersion in the optical constants (n, k) in the measured wavelength range;
  determining the thickness of the thin film and coefficients of the dispersion formula, comprising the optical constants of the unknown layers of the thin film; and
  outputting the optical constants to a user, displaying the optical constants to a user, or storing the optical constants for later use by a user.

15. The method recited in claim 14 which further comprises a nonlinear global optimization algorithm that minimizes a merit function of measured and theoretical data.

16. The method recited in claim 15 wherein the merit function is defined by the equation:

$$\text{Merit Function} = \left[ \sum_{j=1}^{n} \left[ |Y_{\exp j} - Y_{calculated j}|^\beta \times \text{weight}_j \right] \right]^{\frac{1}{\beta}},$$

where $Y_{\exp j}$ and $Y_{calculated j}$ represent the measured and calculated (simulated) data of parameter j, and β=1, 2 for absolute deviation and least squares, respectively.

17. The method recited in claim 15 wherein each fitted parameter has its own merit function that is minimized that is defined by the equation:

$$(\text{Merit Function})_j = \left[ |Y_{target j} - Y_{calculated j}|^\beta \times \text{weight}_j \right]^{\frac{1}{\beta}}.$$

where $Y_{target j}$ and $Y_{calculated j}$ represent the measured data and calculated (simulated) data of parameter j, and β=1, 2 for absolute deviation and least squares, respectively.

* * * * *